United States Patent
Sittinger et al.

(10) Patent No.: US 6,602,294 B1
(45) Date of Patent: Aug. 5, 2003

(54) IMPLANTABLE SUBSTRATES FOR THE HEALING AND PROTECTION OF CONNECTING TISSUE, PREFERABLY CARTILAGE

(75) Inventors: Michael Sittinger, Grossziethen (DE); Olaf Schultz, Berlin (DE); Gerd-Rudiger Burmester, Berlin (DE)

(73) Assignee: TransTissue Technologies GmbH, Berlin ( * ) Notice: Subject to any disclaimer, the term of this patent is extended or adjusted under 35 U.S.C. 154(b) by 34 days.

(21) Appl. No.: 09/718,801

(22) Filed: Nov. 22, 2000

(30) Foreign Application Priority Data

Nov. 24, 1999 (DE) .......................................... 199 57 388

(51) Int. Cl.[7] .................................................. A61F 2/28
(52) U.S. Cl. .................................. 623/23.63; 623/23.61
(58) Field of Search .......................... 623/23.61, 23.62, 623/23.63, 23.76, 66.1, 16.11; 264/28, 344, 41; 514/2, 12; 424/482, 486, 488; 435/6, 174, 325, 180

(56) References Cited

U.S. PATENT DOCUMENTS

| | | | |
|---|---|---|---|
| 5,817,773 A | | 10/1998 | Wilson et al. |
| 5,837,258 A | | 11/1998 | Grotendorst |
| 5,853,746 A | | 12/1998 | Hunziker |
| 5,910,489 A | | 6/1999 | Falk et al. |
| 5,944,754 A | * | 8/1999 | Vacanti |
| 6,080,194 A | * | 6/2000 | Pachence et al. |
| 6,242,247 B1 | * | 6/2001 | Rieser et al. |
| 6,277,151 B1 | * | 8/2001 | Lee et al. |
| 6,334,968 B1 | * | 1/2002 | Shapiro |

FOREIGN PATENT DOCUMENTS

| | | |
|---|---|---|
| EP | 0 312 208 | 4/1989 |
| WO | WO 90/00060 | 1/1990 |
| WO | WO 99/19005 | 4/1999 |
| WO | WO 99/33415 | 7/1999 |

OTHER PUBLICATIONS

W. B. van den Berg, "The role of cytokines and growth factors in cartilage destruction in osteoarthritis and rheumatoid arthritis", Z. Rheumatol 58:136–141 (1999).
J. A. Buckwalter et al., "Articular Cartilage Repair and Transplantation", Arthritis & Rheumatism, vol. 41. No. 8, pp. 1331–1342, (Aug. 1998).
C. H. Evans et al., "Gene Therapy for Rheumatic Diseases", Arthritis & Rheumatism, vol. 42, No. 1, pp. 1–16, (Jan. 1999).
J. H. Herndon et al., "Arthritis: Is the Cure in Your Genes?", The J. of Bone and Joint Surgery, vol. 81–A, No. 2, (Feb. 1999).
J. R. Kalden et al., "Gentherapie der rheumatoiden Arthritis ein bereits anwendbares Therapienprinzip?", Z. Rheumatol 57: 1–8, (1998).
N. R. Kübler, "Osteoinduktion und–reparation", Mud Kiefer GesichtsChir 1:2–25, (1997).
M. Sittinger et al., "Joint cartilage regeneration by tissue engineering", Z. Rheumatol, 58: 130–135, (1999).

* cited by examiner

*Primary Examiner*—Pedro Philogene
(74) *Attorney, Agent, or Firm*—Jones Day

(57) ABSTRACT

Implantable substrate for the healing and/or protection of connecting tissue, preferably cartilage, comprising at least one composition for the activation of locally present cells for tissue regeneration and at least one structure for cell invasion in vivo and/or for the formation of cell matrix and/or for the release of constituents of the employed composition.

5 Claims, 1 Drawing Sheet

Figure 1:
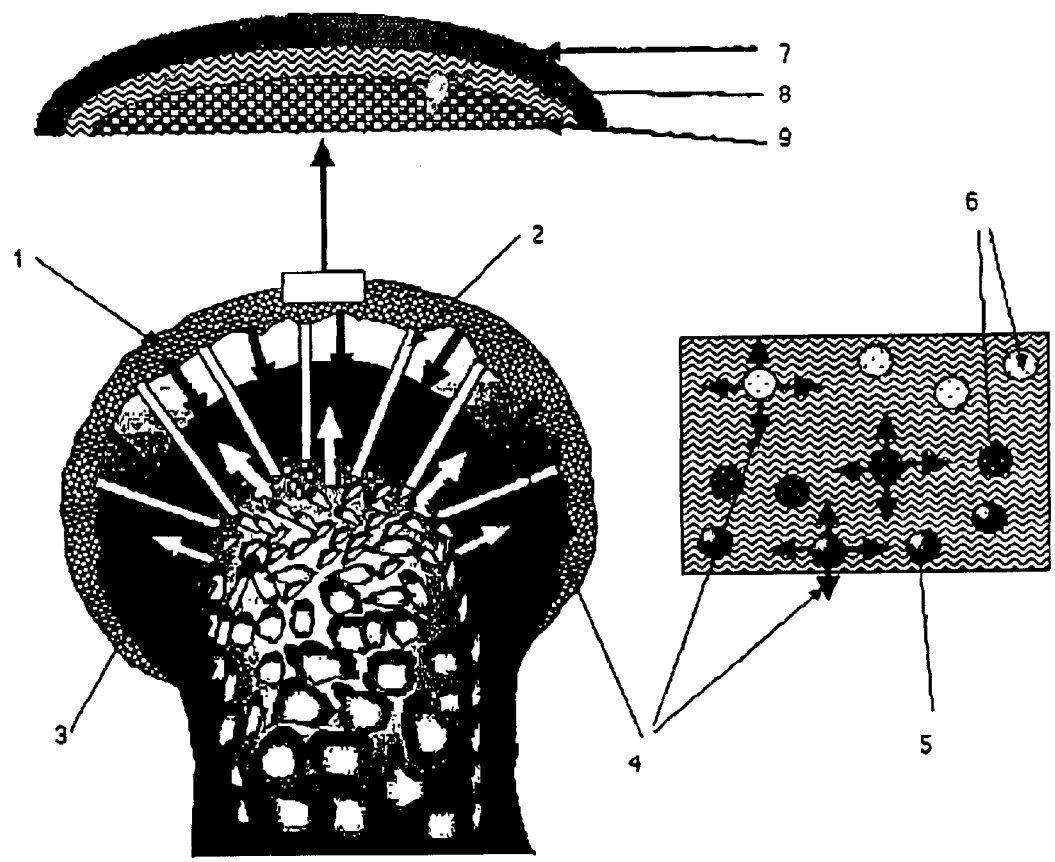

IMPLANTABLE SUBSTRATES FOR THE HEALING AND PROTECTION OF CONNECTING TISSUE, PREFERABLY CARTILAGE

The invention relates to implantable substrates for the healing and protection of connecting tissue, preferably cartilage in the state of athrosis, more specifically, the latter relates to an implantable substrate for the healing and protection of connecting tissue, prefeerably cartilage, comprising at least one structure for the invasion of cells in vivo and/or for the formation of cell matrix and/or for the release of constituents of the employed means and at least one means for the activation of locally present cells for the regeneration of tissue, a method for the production of the latter, a method for the healing and/or protection of connecting tissue, preferably cartilage in the state of arthrosis, employing the substrates according to the invention, as well as the use of the latter in the field of surgical medicine and tissue engineering.

Arthrosis

Osteoarthrosis is the most common joint disease worldwide, the majority of humans older than 65 are affected by the latter. As a necessary consequence, there is an enormous clinical, health-political and economical relevancy of methods directed to the treatment of osteoarthrosis. During the course of this primarily degenerative joint disease, which is dependent on the age, a stepwise focal destruction of the surface of the joint occurs, and, as a reaction, an misregulated regional growth of the neighboring and subchondral bone structures (osteophytes) happens. The consequence is pain and restricted function and mobility. Systemic factors which influence the emergence of osteoarthrosis are age, gender, weight, osteoporosis, hereditary factors and an excess of mechanical stress. Local factors comprise the specific shape of the joint, distortions, traumata, as well as specifically acting biomechanical factors. Although the primary genesis is degenerative, during the course of osteoarthrosis, there are inflammatory degenerations to be observed, such as synovitis (inflammation of the endothelium of the joint) and the production of biological messenger substances, which promote the inflammation, occurs (cytokines and growth factors). These ongoing changes embody an ill-regulated regulation of tissue homeostasis, which occurs in the area of load-carrying cartilage and bone structures, i.e., there is a lack of balance between degenerative processes and repair processes (W B van den Berg: The role of cytokines and growth factors in cartilage destruction in osteoarthritis, Z Rheumatol. 58:136–141, 1999).

The disease is a consequence of malfunctions in the area of the entire joint including the bone, the muscle and the innervation of the joint, which finally leads to an excessive mechanical stress and a biochemically mediated destruction of the affected joints. Furthermore, it is important that there has yet not been any possibility of healing the latter disease: Very often, physiotherapeutic measures and pain-reducing, anti-inflammatory medicaments (non-steroidal anti-rheumatic drugs) are insufficient symptomatic kinds of treatments. Conventional orthopedic measures (debridement, joint-shaving, microfracture, drilling) are also only effective in an insufficient manner. If extensive degenerations occur, often a surgical reconstructive measure with endoprothetic exchange of the joint remains as the only option (J A Buckwalter, H J Mankin: Articular Cartilage Repair and Transplantation: Arthritis & Rheumatism 41:1131–1342, 1998).

Regeneration of Cartilage by Tissue Engineering with Cells and Growth Factors

Tissue engineering offers promising new technologies by transplantation of functionally active autologous cells and optionally of biomaterials creating a desired shape of the material.

Using the latter technology, new cartilage and bone tissue is actively built up or bred, respectively. Usually, tissue engineering is based on the breeding of autologous cells which are subsequently transplanted into the patient, for example as a solution or as a matured graft. Unfortunately, the proliferative potential of these cells is limited and the breeding over many cell passages in vitro substantially reduces the functional quality of the cells.

A further approach in tissue engineering is embodied by the stimulation of tissue regeneration itself or at least the differentiation of cells which were yielded from the patient beforehand, for example by addition of growth factors. In this context, especially the factors of the TGF-β-superfamily are of interest, because they play a major role during the development of tissues and organs. Concerning tissue engineering, there are substantially different principles to employ these factors. For example, a part of the cells may be transfected with the genes of the TGF-β-family to achieve an improved maturation, but also in order to protect the tissue of an, e.g., chronically inflammated joint from being destroyed again (Evans C H, Robbins P D: Gene therapy for arthritis, Gene therapeutics: Methods and applications of direct gene transfer, edited by J A Wolff, Boston, Birkhäuser, 321, (1994); Kalden J R, Geiler T, Hermann M, Bertling W: Gentherapie der rheumatoiden Arthritis—ein bereits anwendbares Therapieprinzip?—Z Rheumatol 57:139–47, (1988); Herndon J H, Robbins P D, Evans C H: Arthritis: is the cure in your genes? J Bone Joint Surg Am, 81:152–7, (1999)).

A further possibility lies in the use of release systems (U.S. Pat. No. 5,910,489), i.e., the transient release of factors from resorbable microparticles or cell carriers, e.g., to stabilize a graft during the critical phase of wound healing. Finally, the direct regeneration of tissue may be achieved without cells by using growth factors and biomaterials (Kübler, Osteoinduktion und-reparation, Mund-Kiefer-Gesichtschir., 1, 2–25, (1997)).

The discovery and characterization of new factors, which are capable of influencing the maturation and differentiation of somatic cells, tools are available which allow for the manufacture of a full-fledged replacement cartilage or bone, starting with only a few autologous cells.

However, the major disadvantage of the latter technology is the necessity to yield a tissue sample from the patient at first and also the comparably sophisticated cultivation of the cells.

Recruitment of Stem Cells, Growth Factors

During a naturally-occurring tissue healing process, normally cells from the surrounding of the defect or lesion are attracted in order to fill that lesion. They are mainly precursor cells which at a later stage develop into tissue cells with their particular properties. Accordingly, when a bone fracture happens, precursor cells from the periostium and the bone marrow migrate into the defect and form new bones via the "detour" of a cartilage tissue. Natural regeneration of cartilage by means of invading precursor cells does finally not work in humans at all. Certain methods of treatment, such as methods of microfracture, are aimed at opening the way into the joint space for cells originating from bone marrow.

In the are of cartilage healing also bioactive substances have been developed, which posses chemotactic, anti-inflammatory, anti-angiogenetic, differentiating or anti-adhesive properties (U.S. Pat. No. 5,853,746: Methods and compositions for the treatment and repair of defects or lesions in cartilage or bone using functional barrier; U.S. Pat. No. 5,817,773: Stimulation, production, culturing and transplantation of stem cells by fibroblast growth factors; U.S. Pat. No. 5,910,489: Topical composition containing hyaluronic acid and NSAIDs).

The invention is based on the problem of developing a substrate which can be used in the process of the healing and/or protection of connecting tissue, preferably cartilage. The problem was solved by the provision of implantable substrates for the healing and/or protection of connecting tissue, particularly for the healing and/or protection of cartilage in the state of arthrosis.

The present invention is particularly based on the use or stimulation, respectively, of pluripotent precursor cells or mesenchymal stem cells for the regeneration of tissue, the potential of which concerning proliferation and differentiation is of major interest for the healing of cartilage and bone. Precursors and stem cells may be used in a comparable manner to the adult cells. Doing so, the differentiation behavior may be influenced by using different morphogenic factors, such as, for example, FGF (fibroblast growth factor) or TGF-$\beta$ (transforming growth factor $\beta$)-superfamily under defined culture parameters (U.S. Pat. No. 5,817,773).

Hence, the present invention relates to an implantable substrate for the healing and/or protection of connecting tissue, preferably cartilage, comprising at least one means for the activation of locally present cells to achieve tissue generation and at least one structure for the invasion of cells in vivo and/or for the formation of cell matrix and/or for the release of constituents of the means employed.

The invention further relates to a substrate for the protection and/or healing of connecting tissue, preferably cartilage, comprising at least one means containing differentiating and chemotactic factors, preferably in combination with a structure such as defined hereinabove.

In the present context, the term "substrate" denominates the entirety of the subject matter according to the invention. The substrate according to the invention may e.g. be a spreadable or adhesive "cell attraction paste" or a kind of "bioactive cartilage covering". One embodiment of the substrate according to the invention is shown in FIG. 1.

The term "structure for cell invasion in vivo and/or for the formation of cell matrix and/or for the release of constituents of the means employed" (structure) comprises the matrix in which the means according to the invention is present.

The term "means" comprises the entirety of usable biologically active and inactive constituents which may be used in the scope of the present invention which in their entirety contribute to the activation of locally present cells for the purpose of tissue regeneration.

"Chemotactic factors" are biologically active factors which are capable of "attracting" cells, for example cartilage precursor cells from bone marrow, autologous mesenchymal cells, progenitor cells and stem cells to the area of treatment or, respectively, to the location, where the substrate according to the invention is located.

"differentiating factors" are biologically active factors, which are capable of inducing cell growth, in particular of the cells mentioned hereinabove, and, concomittantly, the formation of new tissue.

Surprisingly, it was possible to provide a substrate with means, which allows for the induction and control of invasion of tissue precursor cells from the surrounding tissues—in case of the joint cartilage this means from the bone marrow or synovium. This happens by releasing the means contained in the substrate during treatment.

FIG. 1 shows a preferred embodiment of the substrate according to the invention, which is constructed in a sandwich-like manner.

Means

The means used in the scope of the substrate according to the invention are capable of inducing and controlling the invasion of tissue precursor cells from surrounding tissues to the locations of treatment. Normally, the means are substances which are capable of mobilizing and/or activating and/or attracting autologous mesenchymal cells, progenitor cells and stem cells. In particular, the means contain biologically active factors, such as, for example, chemotactic or chemotactic and differentiating factors. In particular, the following have to be named.

Growth and differentiation factors, such as, e.g., factors from the TGF-superfamily, FGF-family, PDGF, IGF, EGF;

cellular adhesion molecules, such as, e.g., integrine, CD44, selectines, proteoglycanes;

synthetic peptides, as, for example, RGD-sequences, e.g., arginine-glycine-aspartic acid;

cytokines;

chemotactic factors, as, e.g., CDMP, CTGF, osteopontine, NO-synthase blockers; or components of the extracellular matrix, such as proteoglycanes, fibronectine, collagen.

Furthermore, the means used according to the invention may comprise—depending on the purpose of use—the following components:

enzymes or precursors thereof, as, for example, proteases, metalloproteinases, cathepsines;

inhibitors of enzymes, such as, for example, THVIP, antibodies or synthetic blockers of the catalytic center;

anti-inflammatory additives, such as, e.g., anti-inflammatory medications and/or factors.

Further, the means may also contain autologous and non-autologous cells, such as, for example, mesenchymal cells, progenitor cells, stem cells/precursor cells, which, in turn, may release the corresponding factors.

In a further embodiment, genes or bioactive factors may be transfected into the cells.

In this context, the release of two or more components of the employed means according to the invention may happen simultaneously or sequentially and/or from two or more phases/components/layers of the substrate or the structure, respectively. Further, the used means according to the invention and/or the used structure according to the invention may comprise facilities for a delayed release of the components.

Structures

Further, the substrates according to the invention contain—in one embodiment necessarily and in a further embodiment optionally—suitable structures to allow for cell invasion in vivo and/or for the formation of cell matrix and/or for the release of constituents of the used means, especially of the factors contained therein.

The structures for in vivo cell invasion according to the invention and/or for the formation of cell matrix and/or for the release of constituents of the used means, especially of the chemotactic and/or differentiating factors preferably comprise hydrogels;

sponges (e.g., made of collagen);

wool- or cotton wool-like structures made of polysaccharides (e.g., cellulose wool, cellulose cotton wool);

natural or synthetic polypeptides (fibrin, polylysine);

plaitings, tissues, or knitted fabrics made of fibers (e.g., fibers of resorbable polymers);

cements (e.g., acrylate cement), bonding sheets (e.g., fibrinogen, coated hyaluronic acid sheets);

ceramic materials or a combination of one or more of these structures.

The structures employed according to the invention—and, hence, also the substrates according to the invention—may possess resorbable or non-resorbable properties. Structures showing resorbable properties, for example, comprise hyaluronic acids, preferably such with a molecular weight of 400–600 kD, poly-alpha-hydroxy acids, collagens, alginates, agaroses, fibrins, biological glass materials or combinations thereof. Structures with non-resorbable properties comprise, for example, ceramic materials or combinations of ceramic materials with structures which exhibit resorbable properties.

Further, the substrate according to the invention may comprise a structure having several substructures. The substructures which are able to store and release the means employed according to the invention or, respectively, particular constituents of these means, comprise layers, droplets/spherelets, or surface coatings. Accordingly, it is, for example, possible that within a grid structure made of ceramic material a hydrogel comprising a means according to the invention is implemented.

Hence, the substrate according to the invention may be constructed as a structure in the shape of a sponge, in the form of beads, membranes, grids, cotton wools, bags/cushions, as a liquid, gel or as a multi-layered material. In the latter case, the substrate comprises, e.g., a wool-like polymer construction, such as, for example, polyglycolid, combined with hyaluronic acid and chemotactic growth factors, as, for example, osteopontine.

In general, the substrates exhibit formable, spreadable or paste-like properties with elastic or plastic mechanical properties, and they are injectable.

The substrate or, respectively, the structure contained therein, if present, may also comprise several phases and/or components and/or layers, which, in turn, may release two or more means.

In a preferred embodiment, mesenchymal stem cells may be mixed with hyaluronic acid and are injected at the place of treatment.

In a particular embodiment, the substrates exhibit a structure, e.g., in form of a multi-layered material for the coverage of the joint surface, which at the underside is fitted with pins, hollow needles or anchoring structures, e.g., a velcro fastener. Further, they may be constructed in a way that at the underside they release e.g. cartilage-digesting enzymes—metallo proteinases, hyaluronidases, cathepsines. The pins, hollow needles or anchoring structures are preferably such that they are resorbable.

In a further embodiment, mesenchymal stem cells and/or other connective tissue precursor cells, e.g., cells of the periostium and of the perichondrium are injected with, e.g., hyaluronic acid in a twin-syringe simultaneously or subsequently with separate syringes.

The implantable substrates according to the invention have the capability to mobilize, activate and/or attract autologous mesenchymal cells, progenitor cells and/or stem cells and to stimulate these cells in a way that lets them proliferate, differentiate and/or mature. Into these cells, genes or the above-mentioned bioactive factors may be transfected.

Method of Production

The manufacture of an implantable substrate for the healing and/or protection of connecting tissue, preferably cartilage, according to the invention is achieved by contacting a structure for the purpose of forming a cell matrix and/or the purpose of cell invasion in vivo and/or the purpose of release of constituents of the used means with at least one means for the activation of locally present cells for the regeneration of tissue, or by contacting differentiating factors and chemotactic factors, if the substrate according to the invention does not comprise a structure in the scope of the invention.

Methods of Treatment

Further, the present invention relates to a method of healing and/or protecting connective tissue, especially in the state of arthrosis, characterized in that the connective tissue is contacted with a substrate according to the invention.

The term "connective tissue" in the scope of the present invention comprises cartilage, bone, tendons and meniscus. In a preferred embodiment, when the method according to the invention is used for the healing and/or protection of cartilage, connecting channels within the subchrondal space of the cartilage are generated before the cartilage is contacted with the substrate.

For example, when a cartilage healing and protection treatment takes place, such substrates may be cemented onto the surface to the joint by using fibrin or acrylate cement and may be fitted accordingly. The fibrin and acrylate cements employed are preferably administered with stored chemotactic growth factors (cartilage derived morphogenic protein or connective tissue growth factor). They are brought onto the joint's surface and are preferably cemented to form an artificial superclot using thrombin. Alternatively, the substrate according to the invention comprises, when using a twin-syringe, in one chamber the means according to the invention, e.g., differentiating and/or chemotactic factors and, in a second chamber, thrombin. In particular, the latter variant is used after a microfracture treatment was performed at the location to be treated, with the possibility of bringing the biologically active substances (means) into the superclot.

The induction of the means and/or the release of the factors are preferably achieved from outside, for example, by magnetic fields, electrical impulses such as current or voltage, movement or the injection of substances.

The substrates according to the invention are preferably implemented after the generation of channels, for example, into the subchondral space, for example by microfractures, drillings, stitches. The connecting channels/drillings between the marrow space and the joint space itself may be generated by a grid of needles which may be a constituent of the structure, or by a velcro fitting-like anchoring structure employed with a grid of needles lying underneath.

The latter method in a preferred embodiment is characterized by the fact that the connecting channels between joint space and bone marrow space are produced, a sticky cartilage-friendly layer is brought onto the arthrotic cartilage, cells from the bone marrow are attracted and are developed into cartilage tissue in a surrounding which temporarily provides nutrition and positive influence within the cemented layer. Doing so, substrates which are capable of providing connections between the joint space and the bone marrow space by multiple preformed tiny drillings/channels are employed, by means of which the invasion of tissue precursor cells from the surrounding tissues is induced and structures for the formation of cell matrix are enabled. It is a property of the above-mentioned method that the substrate comprises structures and/or means which are able to cover a joint's surface, preferably in several layers, thereby inducing growth and maturing of cartilage precursor cells from bone marrow.

The substrate according to the invention exhibits a combination of known (mesenchymal cells, progenitor cells, stem cells/precursor cells from bone marrow, bioactive factors) and new elements (connecting channels between bone marrow space and joint space; multi-layered materials for the coverage of the joint's inducing growth and maturing of cartilage precursor cells from bone marrow; artificial superclot) which mutually influence and, by means of their new effect, provide an advantage (synergistic effect) and the desired success, which lies in the fact that cells from bone marrow can now be attracted and develop into cartilage tissue within the substrate according to the invention, e.g., in multi-layered substrates for the coverage of the joint's surface. By using the substrate according to the invention, it is possible to minimize the external breeding and subsequent transplantation of the bred cells into the patients, preferably the latter process can be completely replaced.

The use of the substrates according to the invention is embodied by their employment in surgical medicine and tissue engineering, in particular in the field of cartilage healing and protection in the state of arthrosis, as well as their use for the purpose of proliferation, differentiation and maturation of cells.

The invention shall be further explained by means of worked examples.

EXAMPLES

Example 1

In order to treat a substantially arthrotically deformed joint surface, at first, by using multiply tiny drillings (1–2 mm), small connections between the bone marrow space and the joint space are generated. Subsequently, a wool-like polymer construct (polyglycolid) combined with hyaluronic acid and chemotactic growth factors (osteopontine) are glued onto the joint's surface using fibrin or acrylate cement.

Example 2

In order to treat the joint surface shown in Example 1, after the generation of the connections to the bone marrow space, fibrin cement with stored chemotactic growth factors (cartilage derived morphogenetic protein or connective tissue growth factor) is spread over the joint's surface and is cemented using thrombin (artificial superclot).

List of Abbreviations

CD44—cluster of differentiation
CDMP—cartilage derived morphogenetic protein
CTGF—connective tissue growth factor
EGF—epidermal growth factor
FGF—fibroblast growth factor
IGF—insulin-like growth factor
NO-synthase-inhibitor—nitrogen oxide synthase inhibitor
NSAID—non-steroidal anti-inflammatory drugs
PDGF—platelet derived growth factor (growth factor formed by thrombocytes)
RGD-sequences—arginine-glycine-aspartic acid sequences
PVC—polyvinyl chloride
TGF-β-superfamily—transforming growth factor beta superfamily
TIMP—tissue inhibitor of metalloproteinases.

For FIG. 1

1: substance spread
2: connecting channels to the bone marrow
3: migration of precursor cells out of the bone marrow
4: release of bioactive factors
5: mesenchymal cells, optionally genetically modified
6: particles with bioactive factors
7: covering layer
8: layer composed of differentiating or tissue-forming, respectively, factors
9: layer with chemotactic factors

What is claimed is:

1. An implantable substrate for the healing and/or protection of a connecting tissue, comprising:
   a composition comprising the biologically active factors (i), (ii), and (iii), wherein
      (i) is a growth and differentiating factor,
      (ii) is a chemotactic factor, and
      (iii) is a cellular adhesion molecule; and
   at least one structure for cell invasion in vivo and/or for the formation of cell matrix and/or for the release of constituents of the employed composition, wherein said structure comprises at least one constituent (a) to (f):
      (a) a hydrogel,
      (b) a compound selected from the group consisting of sponges, collagen sponges,
      (c) a compound selected from the group consisting of wool, a cotton wool-like structure, wool made of polysaccharides, cellulose wool, and cellulose cotton wool,
      (d) a compound selected from the group consisting of natural or synthetic polypeptides, fibrin, and polylysine,
      (e) a compound selected from the group consisting of plaitings, knitted fabrics, woolen structures made of fibers, and fibers comprising resorbable polymers,
      (f) a compound selected from the group consisting of cement pastes, acrylate cements, bonding sheets, and fibrinogen-covered hyaluronic acid foil.

2. The substrate of claim 1, wherein said connecting tissue comprises cartilage.

3. The substrate of claim 1, wherein said substrate further comprises at least one covering material.

4. The substrate of claim 1, wherein said composition contains at least one biologically active factor chosen from the group consisting of synthetic peptides, cytokines, and extra cellular matrix components.

5. The substrate of claim 1, further comprising an anchoring structure for anchoring said substrate in or on the location to be treated.

* * * * *